(12) United States Patent
Higashiyama et al.

(10) Patent No.: US 12,247,570 B2
(45) Date of Patent: Mar. 11, 2025

(54) CPAP DEVICE

(71) Applicant: Murata Manufacturing Co., Ltd., Kyoto (JP)

(72) Inventors: Yuzo Higashiyama, Kyoto (JP); Takahiro Yamaguchi, Kyoto (JP)

(73) Assignee: MURATA MANUFACTURING CO., LTD., Kyoto (JP)

( * ) Notice: Subject to any disclaimer, the term of this patent is extended or adjusted under 35 U.S.C. 154(b) by 241 days.

(21) Appl. No.: 18/047,313

(22) Filed: Oct. 18, 2022

(65) Prior Publication Data

US 2023/0114545 A1  Apr. 13, 2023

Related U.S. Application Data

(63) Continuation of application No. PCT/JP2021/018256, filed on May 13, 2021.

(30) Foreign Application Priority Data

May 15, 2020 (JP) ................ 2020-086002

(51) Int. Cl.
F04D 25/06 (2006.01)
F04D 29/58 (2006.01)

(52) U.S. Cl.
CPC ......... F04D 25/0606 (2013.01); F04D 29/58 (2013.01); *F04D 25/062* (2013.01)

(58) Field of Classification Search
CPC .. H02K 9/16; H02K 9/14; H02K 9/08; H02K 9/02; H02K 5/207; H02K 5/203;

(Continued)

(56) References Cited

U.S. PATENT DOCUMENTS

2009/0062020 A1* 3/2009 Edwards ............... F04D 13/027
                                                     415/122.1
2010/0319697 A1  12/2010 Farrugia et al.
(Continued)

FOREIGN PATENT DOCUMENTS

JP  H03-207724 A   9/1991
JP  2008-518646 A  6/2008
(Continued)

OTHER PUBLICATIONS

International Search Report for PCT/JP2021/018256 dated Jul. 6, 2021.

*Primary Examiner* — Ahmed Elnakib
(74) *Attorney, Agent, or Firm* — McDonald Hopkins LLC (57) ABSTRACT

The CPAP device includes a blower. The blower includes a motor and a blower fan rotatable by the motor. The motor includes a stator assembly including a plurality of coils arranged in a circumferential direction, and a rotor assembly including a permanent magnet and disposed in an inner side portion of the stator assembly in a radial direction. An output shaft is inserted into the rotor assembly. The output shaft rotates together with the rotor assembly. The blower fan is fixed to a tip end of one side of the output shaft. Part of the output shaft is inserted into an insertion hole provided at a center of the base. A plain bearing is interposed between an inner peripheral surface of the insertion hole and an outer peripheral surface of the output shaft.

10 Claims, 5 Drawing Sheets

(58) Field of Classification Search
CPC ....... H02K 5/20; F04D 25/0606; F04D 29/58; F04D 25/062; F04D 29/023; F04D 29/281; F04D 29/5853; F04D 29/4226; F05D 2300/224; F05D 2260/22141; F05D 2300/44; F05D 2300/5024; A61M 16/00
USPC .......................................................... 310/58
See application file for complete search history.

(56) References Cited

U.S. PATENT DOCUMENTS

| | | | |
|---|---|---|---|
| 2013/0306072 A1* | 11/2013 | Moir | F04D 29/048 |
| | | | 415/203 |
| 2014/0112805 A1 | 4/2014 | Sakai | |
| 2017/0268524 A1* | 9/2017 | Kanai | F04D 29/056 |
| 2018/0177373 A1* | 6/2018 | Hayamitsu | F04D 29/162 |
| 2020/0155778 A1* | 5/2020 | Kuriger | A61M 16/109 |
| 2023/0114545 A1* | 4/2023 | Higashiyama | F04D 29/58 |
| | | | 310/58 |
| 2024/0178717 A1* | 5/2024 | Hwang | F16C 25/083 |

FOREIGN PATENT DOCUMENTS

| | | |
|---|---|---|
| JP | 2009-057967 A | 3/2009 |
| JP | 2014-0508594 A | 4/2014 |
| JP | 2014-084755 A | 5/2014 |
| JP | 2014080913 A | 5/2014 |
| JP | 2019-078195 A | 5/2019 |

* cited by examiner

CPAP DEVICE

CROSS REFERENCE TO RELATED APPLICATION

This is a continuation of International Application No. PCT/JP2021/018256 filed on May 13, 2021 which claims priority from Japanese Patent Application No. 2020-086002 filed on May 15, 2020. The contents of these applications are incorporated herein by reference in their entireties.

BACKGROUND OF THE DISCLOSURE

Field of the Disclosure

The present disclosure relates to a continuous positive airway pressure (CPAP) device (hereinafter described as CPAP device).

Description of the Related Art

The CPAP device described in Patent Document 1 includes a blower to supply gas. A motor is built in the blower. A blower fan is attached to an output shaft of the motor. When the output shaft of the motor rotates, the blower fan also rotates together with the output shaft. Then, the rotation of the blower fan sends air.

Patent Document 1: Japanese Unexamined Patent Application Publication (Translation of PCT Application) No. 2008-518646

BRIEF SUMMARY OF THE DISCLOSURE

In the CPAP device disclosed in Patent Document 1, components included in the motor, such as a coil, generate heat with the rotation of the motor. Since the performance of the motor may decline due to the heat generation of the coil or the like, it is necessary to efficiently exhaust the heat in the motor. However, in the CPAP device disclosed in Patent Document 1, no consideration is given to the exhaustion of the heat of the motor, and there is still room for improvement.

An aspect of the present disclosure to solve the above issue is the CPAP device below. The CPAP device includes a housing, a motor accommodated in the housing, and a blower fan rotatable by the motor. The motor includes a stator assembly including a plurality of coils arranged in a circumferential direction, a rotor assembly including a permanent magnet and disposed in an inner side portion of the stator assembly in a radial direction, an output shaft fixed to the rotor assembly and configured to rotate together with the rotor assembly, and a base having an insertion hole into which part of the output shaft is inserted and supporting the output shaft. The stator assembly is fixed to the base, a plain bearing is interposed between an inner peripheral surface of the insertion hole and an outer peripheral surface of the output shaft, and the blower fan is fixed to the output shaft.

According to the configuration described above, since the plain bearing is provided between the inner peripheral surface of the insertion hole and the outer peripheral surface of the output shaft, it is possible to increase a contact area between the inner peripheral surface of the insertion hole and the outer peripheral surface of the output shaft in comparison with a case that the output shaft is supported by a rolling bearing, for example. Accordingly, part of the heat generated by energizing the coil is transferred to the output shaft through the base. Further, since the blower fan is fixed to the output shaft, the heat transferred to the output shaft is dissipated by the blower fan. That is, according to the configuration above, by ensuring a heat transfer path from the stator assembly to the blower fan, the blower fan is caused to function also as a member for heat dissipation. Thus, heat exhaust performance is improved.

According to an aspect of the present disclosure, the heat exhaust performance of a motor may be improved.

DETAILED DESCRIPTION OF THE DISCLOSURE

Hereinafter, an embodiment of a CPAP device configured to send air introduced into the device to an airway of a user will be described with reference to the accompanying drawings.

Figure 1:
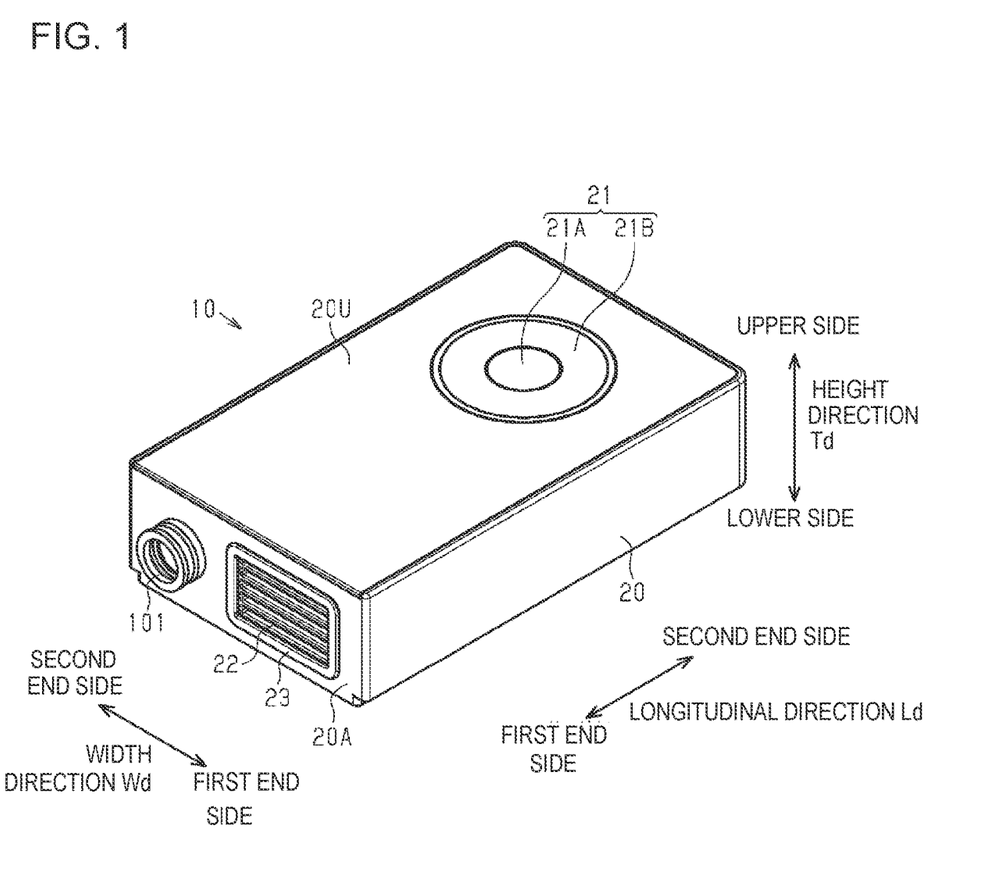
FIG. 1 is a perspective view of a CPAP device.

As illustrated in FIG. 1, a CPAP device 10 includes a housing 20 having a flat rectangular parallelepiped shape. A material of the housing 20 is a synthetic resin such as acrylonitrile-butadiene-styrene resin, polycarbonate, or phenol resin. Note that, in the following description, a thickness direction of the housing 20 is referred to as a height direction Td. Further, when viewed in the height direction Td, a longitudinal direction of the housing 20 is referred to as a longitudinal direction Ld, and a lateral direction of the housing 20 is referred to as a width direction Wd.

An operation portion 21 for operating the CPAP device 10 is provided on an upper side surface 20U, which is a surface of the housing 20 on an upper side in the height direction Td. In this embodiment, the operation portion 21 is constituted of a switch 21A having a circular shape and a switch 21B having an annular shape. The switch 21B is disposed to surround the switch 21A. Both the switch 21A and the switch 21B are push button switches, and by operating these switches, it is possible to turn on and off a power supply of the CPAP device 10, to change settings, and the like.

An inhalation port 22 for introducing air from the outside of the housing 20 to the inside opens in a first end surface 20A, being an end surface of the housing 20 on a first end side in the longitudinal direction Ld. A filter 23, for filtering out dust and the like contained in the air introduced into the housing 20, is attached to the inhalation port 22.

Figure 2:
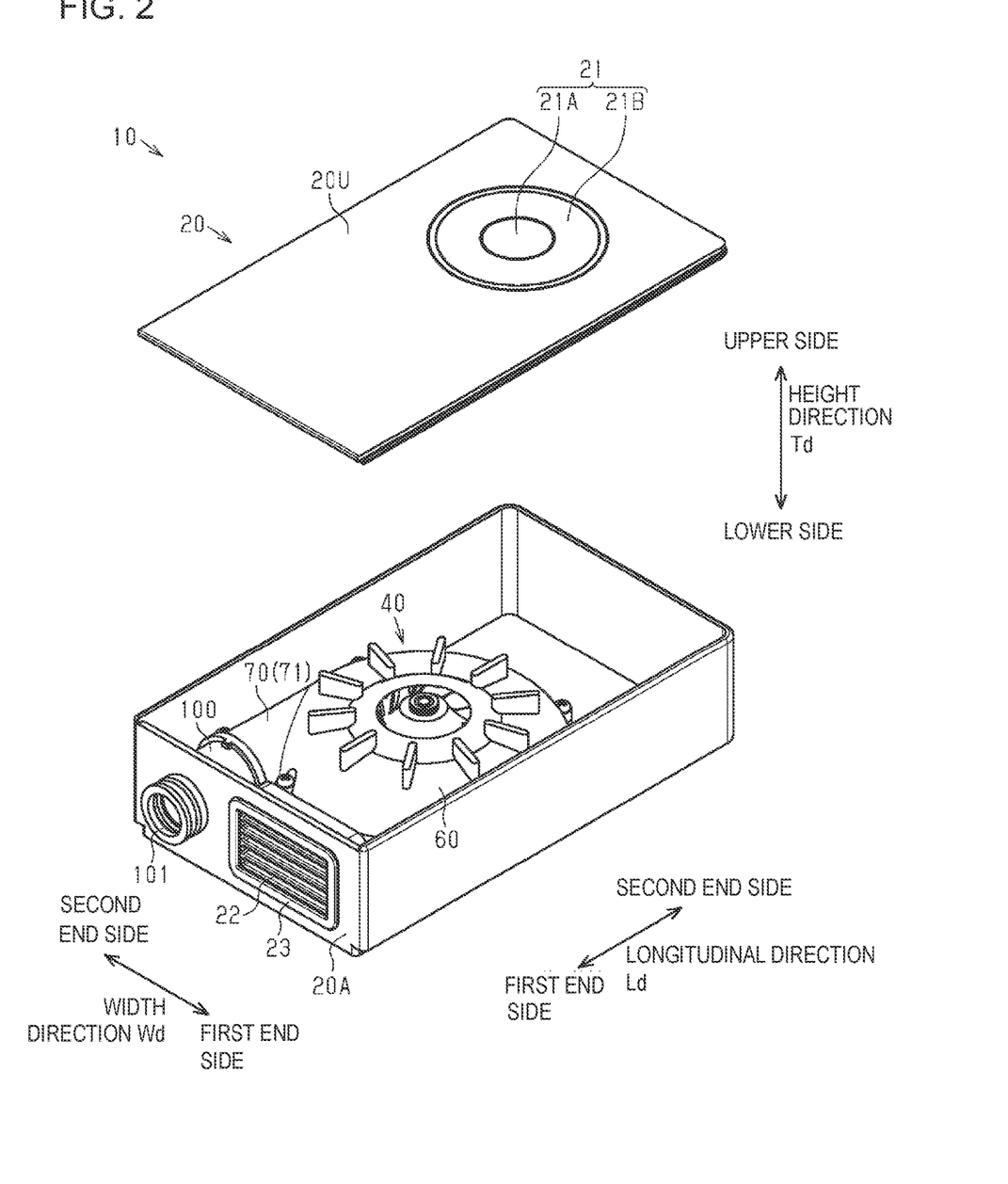
FIG. 2 is an exploded perspective view of the CPAP device.
Figure 3:
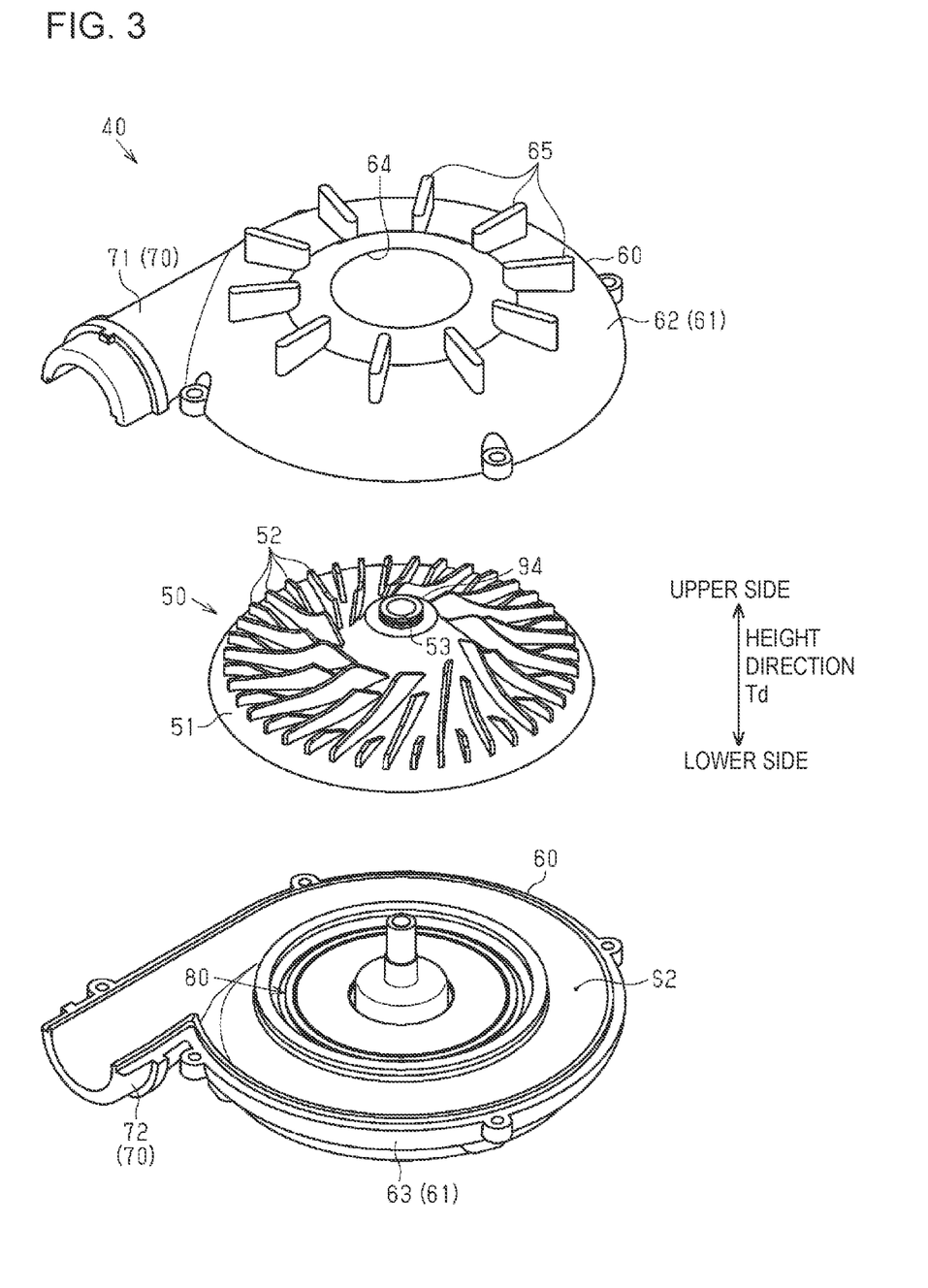
FIG. 3 is an exploded perspective view of a blower fan in the CPAP device.

As illustrated in FIG. 2, a blower 40 is accommodated inside the housing 20. The blower 40 is disposed close to the first end side of the housing 20 in the longitudinal direction Ld. As illustrated in FIG. 3, the blower 40 includes a motor 80, a blower fan 50, and a fan case 61 to cover the blower fan 50.

As illustrated in FIG. 3, the fan case 61 includes an upper fan case 62 and a lower fan case 63. The lower fan case 63 is fitted to the lower side of the upper fan case 62 to face each other. Further, the fan case 61 is roughly divided into a fan portion 60 having a substantially annular shape and a lead-out tube 70 protruding from the fan portion 60.

As illustrated in FIG. 3, the fan portion 60 of the upper fan case 62 has a substantially circular bowl shape. An inlet port 64 for inhaling air to the inside of the fan case 61 opens at a center of the fan portion 60 in the upper fan case 62. The inlet port 64 has a circular shape in a plan view. A projection wall 65 having a plate shape projects upward from an upper side outer surface of the upper fan case 62. The plurality of projection walls 65 is provided, and in the present embodiment, ten projection walls 65 are provided. The projection wall 65 extends in a radial direction of the upper fan case 62. Further, the projection walls 65 are arranged at equal intervals in a circumferential direction at the outer side portion of the inlet port 64 in the radial direction.

The fan portion 60 in the lower fan case 63 has a substantially annular shape when viewed in the height direction Td. An outer diameter of the fan portion 60 in the lower fan case 63 is equal to an outer diameter of a lower edge of the fan portion 60 in the upper fan case 62. The fan portion 60 in the lower fan case 63 has a shape of a semicircle protruding downward in a section orthogonal to the radial direction. The motor 80 is fitted into a hole at the center of the fan portion 60 in the lower fan case 63. Note that the motor 80 will be described in detail later.

As illustrated in FIG. 3, the lead-out tube 70 having a substantially circular tube shape is connected to the fan portion 60. The lead-out tube 70 is constituted of an upper tube portion 71 and a lower tube portion 72.

The upper tube portion 71 extends from the fan portion 60 in the upper fan case 62 toward the first end side in the longitudinal direction Ld. When viewed in the extending direction of the upper tube portion 71, the upper tube portion 71 has a shape of an arc protruding upward. That is, the upper tube portion 71 constitutes an upper half of the lead-out tube 70 having a substantially circular tube shape. Note that, in the present embodiment, the upper tube portion 71 is integrally molded with the upper fan case 62.

The lower tube portion 72 extends from the fan portion 60 in the lower fan case 63 toward the same direction as the upper tube portion 71. When viewed in the extending direction of the lower tube portion 72, the extension length of the lower tube portion 72 is equal to that of the upper tube portion 71. When viewed in the extending direction, the lower tube portion 72 has a shape of an arc protruding downward. That is, the lower tube portion 72 constitutes a lower half of the lead-out tube 70 having a substantially circular tube shape. Note that, in the present embodiment, the lower tube portion 72 is integrally molded with the lower fan case 63.

As illustrated in FIG. 2, a discharge tube 100 for discharging air from the inside of the housing 20 to the outside is connected to the lead-out tube 70. The discharge tube 100 has a circular tube shape. The discharge tube 100 is contiguously connected to an end of the lead-out tube 70 in a direction of air flowing downstream.

The discharge tube 100 penetrates through the first end surface 20A of the housing 20, and extends in the longitudinal direction Ld. An end of the discharge tube 100 on the first end side in the longitudinal direction Ld is, therefore, positioned at an outer side portion of the housing 20. An opening of the discharge tube 100 on the first end side in the longitudinal direction Ld is a discharge port 101 for discharging air from the inside of the housing 20 to the outside.

Figure 6:
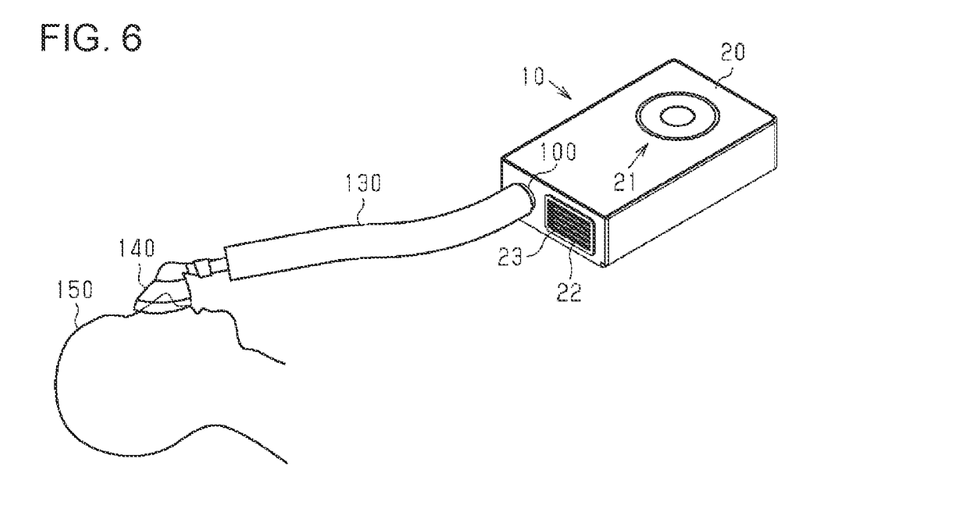
FIG. 6 is an explanatory diagram to describe a usage of the CPAP device.

As illustrated in FIG. 6, when the CPAP device 10 is used, a mask 140 is coupled to the tip end portion of the discharge tube 100 extending to the outside of the housing 20 via a hose 130. The mask 140 is worn to cover the nose or mouth of a user 150, for example.

Figure 4:
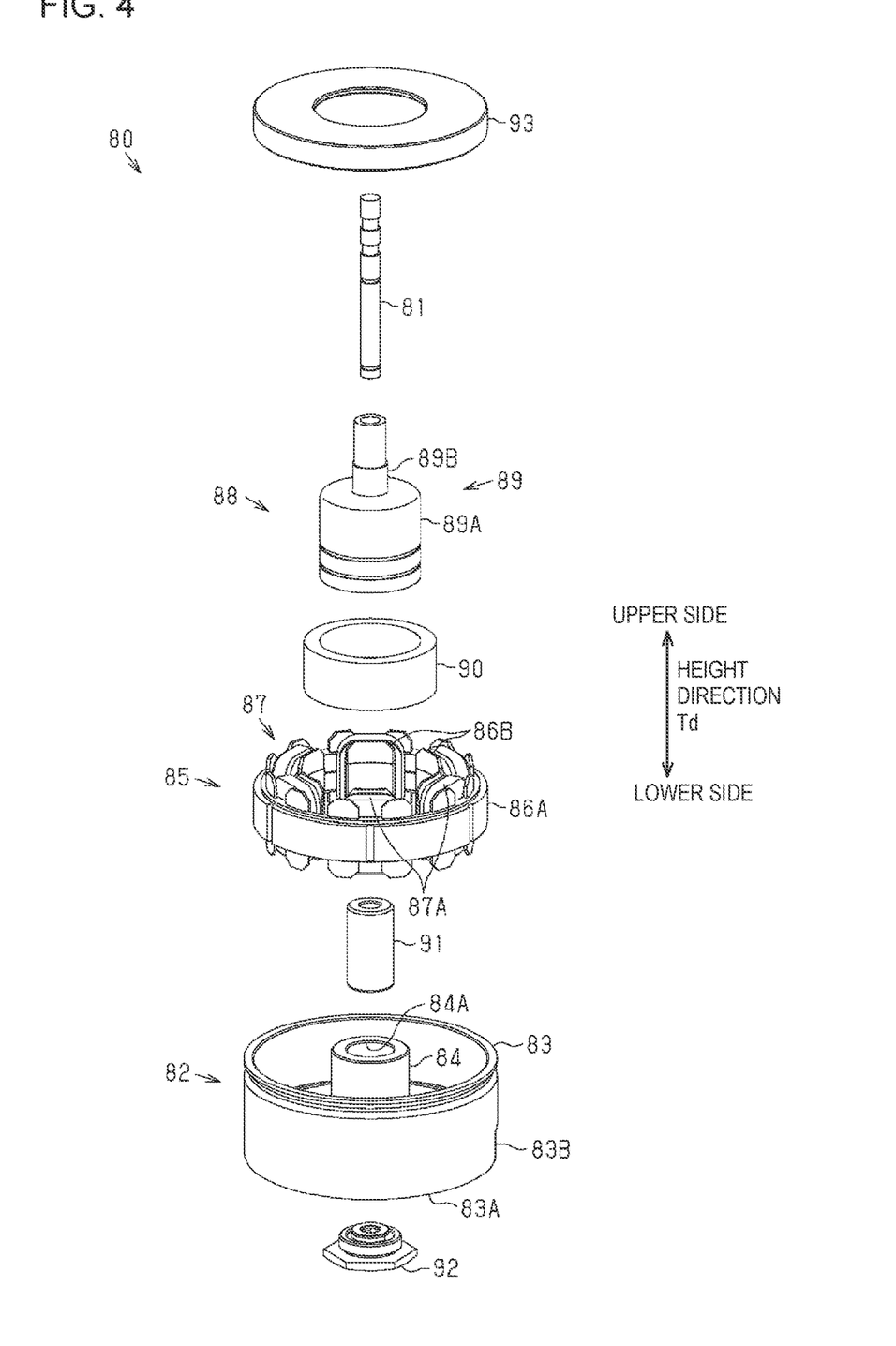
FIG. 4 is an exploded perspective view of a motor in the CPAP device.

As illustrated in FIG. 4, the motor 80 includes a base 82 to accommodate and support constituting components of the motor 80. A main body portion 83 of the base 82 has a bottomed cylindrical shape as a whole. That is, the main body portion 83 has a shape in which a side portion 83B protrudes upward in the height direction Td from an edge of a circular bottom portion 83A. A pivotally support portion 84 protrudes upward in the height direction Td from a center of the bottom portion 83A. The pivotally support portion 84 has a cylindrical shape with an insertion hole 84A penetrating through a center thereof. Further, the insertion hole 84A penetrates through the bottom portion 83A of the main body portion 83. Note that, in the present embodiment, the main body portion 83 and the pivotally support portion 84 are integrally molded. In the present embodiment, a material of the base 82 is an aluminum alloy.

Figure 5:
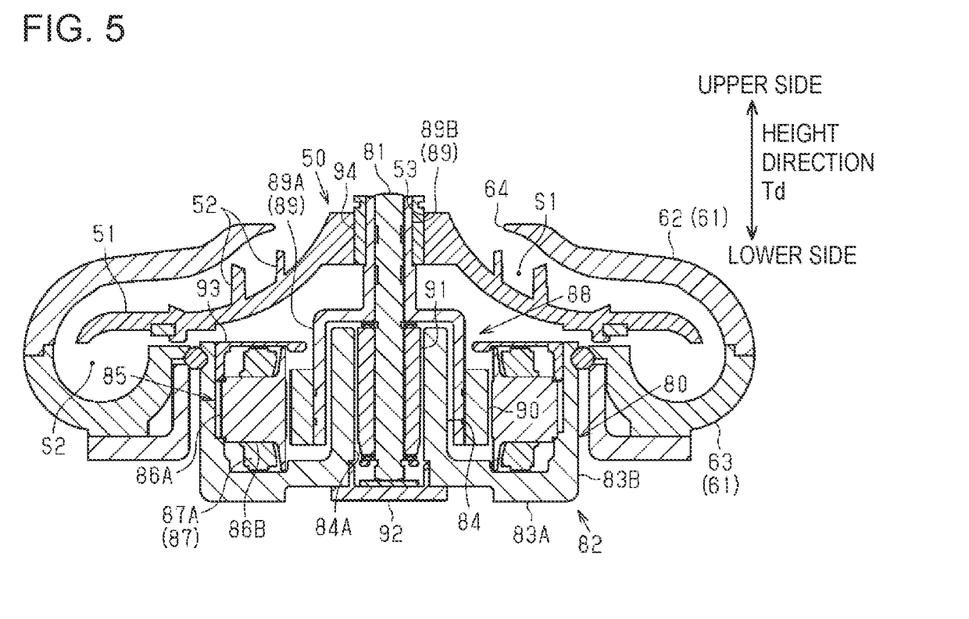
FIG. 5 is a cross-section view of a blower in the CPAP device.

As illustrated in FIG. 4 and FIG. 5, a stator assembly 85 having an annular shape as a whole is disposed in a space between the pivotally support portion 84 and the side portion 83B, in the base 82. A stator yoke 86A in the stator assembly 85 has an annular shape. A surface of the stator yoke 86A on an outer side portion in the radial direction is fixed to a surface of the side portion 83B on an inner side portion in the radial direction.

From a surface of the stator yoke 86A on an inner side portion in the radial direction, teeth 86B protrude toward an inner side portion in the radial direction. The six teeth 86B are provided. The six teeth 86B are arranged at equal intervals in a circumferential direction of the stator yoke 86A. A coil 87 is attached to each of the teeth 86B. The coil 87 is constituted of a winding wire 87A wound around the teeth 86B. The stator yoke 86A and the teeth 86B are made of an electromagnetic steel sheet such as a silicon steel sheet, for example.

As illustrated in FIG. 4 and FIG. 5, a rotor assembly 88 is disposed on an inner side of the stator assembly 85 in the radial direction. The rotor assembly 88 includes a rotor yoke 89 and a permanent magnet 90 that have a cylindrical shape as a whole. The rotor yoke 89 is constituted of a large-diameter portion 89A on a lower side in the height direction Td and a small-diameter portion 89B on the upper side in the height direction Td. An outer diameter and an inner diameter of the small-diameter portion 89B are smaller than an outer diameter and an inner diameter of the large-diameter portion 89A. As illustrated in FIG. 5, the inner diameter of the small-diameter portion 89B is smaller than an outer diameter of the pivotally support portion 84. Further, the inner diameter of the large-diameter portion 89A is larger than the outer diameter of the pivotally support portion 84. The pivotally support portion 84 is accommodated in the large-diameter portion 89A. Further, an inner peripheral surface of the large-diameter portion 89A and an outer peripheral surface of the pivotally support portion 84 in the rotor assembly 88 face each other with no other member interposed therebetween.

As illustrated in FIG. 4 and FIG. 5, the permanent magnet 90 having an annular shape is fixed to a surface of the large-diameter portion 89A of the rotor yoke 89 on an outside portion in the radial direction. The permanent magnet 90 is magnetized such that the poles on the outer side portion in the radial direction are different in every 90 degrees in the circumferential direction. The permanent magnet 90 faces the coil 87 in the radial direction. Further, in the present embodiment, the permanent magnet 90 constituting part of the outer peripheral surface of the rotor assembly 88 faces the coil 87 of the rotor yoke 89 with no other member interposed therebetween.

A rod-shaped output shaft 81 is press-fitted into an inner side portion of the small-diameter portion 89B of the rotor yoke 89 in the radial direction. Part of a lower side of the output shaft 81 in the height direction Td reaches an inside of the large-diameter portion 89A. Then, the part of the lower side of the output shaft 81 in the height direction Td is inserted into the insertion hole 84A of the pivotally support portion 84 on an inner side portion of the large-diameter portion 89A in the radial direction. Further, a plain bearing 91 is interposed between an outer peripheral surface of the output shaft 81 and an inner peripheral surface of the insertion hole 84A.

The plain bearing 91 has a cylindrical shape. An outer diameter of the plain bearing 91 is substantially the same as a diameter of the insertion hole 84A. Further, an inner diameter of the plain bearing 91 is larger than an outer diameter of the output shaft 81 by about several micrometers to several tens of micrometers. A lubricant is filled in a small gap between an inner surface of the plain bearing 91 and the output shaft 81.

A size of the plain bearing 91 in an axial direction is approximately 45% of the entire length of the output shaft 81. In this embodiment, a portion of the output shaft 81 accommodated in the large-diameter portion 89A of the rotor yoke 89 is covered with the plain bearing 91. A nut 92 is disposed on a lower side relative to the plain bearing 91 in the height direction Td. The nut 92 caps the insertion hole 84A of the pivotally support portion 84 from the lower side. The output shaft 81 is supported by the nut 92 from the lower side. Further, the nut 92 suppresses the leakage of the lubricant filled between the output shaft 81 and the plain bearing 91 to the lower side of the plain bearing 91 in the height direction Td.

A flange 93 having an annular shape covers an opening edge of the base 82 on the upper side in the height direction Td. An inner diameter of the flange 93 is slightly larger than an outer diameter of the large-diameter portion 89A of the rotor yoke 89. Note that the output shaft 81 is inserted through a hole at a center of the flange 93, and protrudes to an upper side relative to the flange 93 in a state that the output shaft 81 is covered by the small-diameter portion 89B.

As illustrated in FIG. 5, the blower fan 50 is attached to a tip end portion of the output shaft 81 on the upper side in the height direction Td, through the small-diameter portion 89B of the rotor yoke 89 and a cylindrical body 94. The cylindrical body 94 is a metal member having a cylindrical shape, and is attached to the outer peripheral surface of the small-diameter portion 89B of the rotor yoke 89. As illustrated in FIG. 3 and FIG. 5, the blower fan 50 is constituted of a holding plate 51 and a plurality of blades 52. The holding plate 51 has a substantial disk shape. In this embodiment, the holding plate 51 has a shape that rises upward toward the center. A circular penetration hole 53 opens at a center of the holding plate 51. The output shaft 81 is fixed to the penetration hole 53 through the cylindrical body 94 and the small-diameter portion 89B.

As illustrated in FIG. 3, the plurality of blades 52 protrudes toward the upper side on an upper side surface of the holding plate 51. The blade 52 has a plate shape. The blade 52 extends from the inner side portion of the holding plate 51 toward the outer side portion in the radial direction. Note that, in this embodiment, the blades 52 having different extension lengths are provided. Further, the blades 52 are disposed at equal intervals in a circumferential direction of the holding plate 51. Accordingly, the plurality of blades 52 is radially disposed when viewed in the height direction Td.

The blower fan 50 is formed of a material obtained by mixing a thermosetting synthetic resin as a base material and carbon powder as a heat dissipation material. Note that the carbon powder has higher thermal conductivity than the synthetic resin.

As illustrated in FIG. 5, defined are an accommodation space S1 in which the blower fan 50 is accommodated and a flow passage S2 through which the air blown from the blower fan 50 flows, inside the fan portion 60 in the fan case 61. The accommodation space S1 is configured by a center portion of the internal space of the fan portion 60 in the radial direction. Specifically, the accommodation space S1 is a space vertically sandwiched between an upper surface of the flange 93 and an inner surface of the upper fan case 62. Accordingly, the accommodation space S1 directly communicates with the outside of the fan case 61 through the inlet port 64. The flow passage S2 is configured of the outer side portion of the internal space of the fan portion 60 in the radial direction. Specifically, the flow passage S2 is a space vertically sandwiched between an inner surface of the lower fan case 63 and the inner surface of the upper fan case 62. Accordingly, the flow passage S2 extends in an annular shape manner in an outer side portion of the accommodation space S1 in the radial direction. Further, the flow passage S2 communicates with the accommodation space S1 in the radial direction. In this embodiment, the flow passage S2 has a substantially circular shape in a sectional view orthogonal to the extension direction of the flow passage S2.

When the motor 80 is assembled to the fan case 61, the flow passage S2 is disposed at a position overlapping with the stator assembly 85 in an axial direction of the output shaft 81 and an outer side portion of the stator assembly 85 in the radial direction. In this embodiment, a substantially lower half of the flow passage S2 in the height direction Td is disposed at the position overlapping with the stator assembly 85.

Next, operations of the present embodiment will be described.

When electric power is supplied to the motor 80, the rotor assembly 88 rotates by the electromagnetic force generated between the coil 87 and the permanent magnet 90. With the rotation of the rotor assembly 88, the output shaft 81 and the blower fan 50 rotate. When the blower fan 50 rotates, the air outside of the blower 40 is suctioned to an inside of the fan case 61 through the inlet port 64. The air is guided to the flow passage S2 in the fan case 61 by the centrifugal force of the blower fan 50. The air flows through the flow passage S2 in the circumferential direction as the blower fan 50 rotates. Note that, in the flow passage S2, the flow velocity and pressure of the air are increased by the rotation of the blower fan 50. The air that has passed through the flow passage S2 passes through the lead-out tube 70 and the discharge tube 100, and is discharged to the outside of the blower 40.

Further, when electric power is supplied to the motor 80, an electric current flows through the winding wire 87A of the coil 87. The coil 87 generates heat with the current flowing through the winding wire 87A. The heat of the coil 87 is transferred to members such as the base 82 disposed in the vicinity of the coil 87. The heat of the base 82 is dissipated from the pivotally support portion 84 or from the side portion 83B of the main body portion 83.

The heat transferred to the pivotally support portion 84 is transferred to the plain bearing 91 in contact with the pivotally support portion 84. Further, the heat of the plain bearing 91 is transferred to the output shaft 81 in contact with an inner peripheral surface of the plain bearing 91. Further, the blower fan 50 is attached to the output shaft 81. Since carbon powder is mixed in the blower fan 50, heat is easily transferred. Accordingly, heat is dissipated from the blower fan 50. Further, the heat transferred to the side portion 83B of the main body portion 83 is also transferred to the fan case 61 disposed on an outer side portion of the side portion 83B in the radial direction. In particular, the heat is transferred to the fan case 61 at a portion that defines the flow passage S2 disposed at a position overlapping with the stator assembly 85 in the axial direction of the output shaft 81. That is, heat is transferred from the stator assembly 85 to the lower fan case 63.

Next, effects of the present embodiment will be described.

(1) In the present embodiment, the output shaft 81 is supported by the base 82 through the plain bearing 91. Here, a product having a long size in the axial direction is common for the plain bearing 91 compared with a rolling bearing. On an assumption of a case that the rolling bearing having a long size in the axial direction is adopted, since the rolling bearing is large in the radial direction, there arises a drawback that an outer diameter of a motor becomes large.

In the present embodiment, the plain bearing 91 has a length of approximately 45% of the entire length of the output shaft 81. Accordingly, in a case that the plain bearing 91 is adopted, it is easy to ensure a contact area between the output shaft 81 and the base 82 while preventing the expansion of the motor 80. When the contact area between the output shaft 81 and the base 82 increases, the heat transferred from the coil 87 to the base 82 is easily transferred to the output shaft 81. Moreover, in the embodiment described above, since the lubricant is filled between the outer peripheral surface of the output shaft 81 and the inner peripheral surface of the plain bearing 91, the heat is also transferred through the lubricant. When heat is transferred to the output shaft 81, the heat is also transferred to the blower fan 50 attached to the output shaft 81, and the heat is dissipated through the blower fan 50 or the like. As described above, by ensuring a heat transfer path from the stator assembly 85 to the blower fan 50, the blower fan 50 also functions as a member for heat dissipation, and heat exhaust performance is increased.

(2) When electric power is supplied to the motor 80, the blower fan 50 rotates. Accordingly, while electric power is supplied to the motor 80, fresh air is constantly supplied to the blower fan 50. Thus, by discharging heat from the blower fan 50, efficient heat exhaustion may be expected.

In the present embodiment, carbon powder is mixed in the blower fan 50 made of a synthetic resin as a base material. The heat transfer property of the blower fan 50 containing the carbon powder, therefore, is improved in comparison with a case that the carbon powder is not contained.

(3) Fresh air is supplied to the flow passage S2 in the fan case 61, and in addition to that, the flow velocity of the air flowing through the flow passage S2 is also increased. Accordingly, the fan case 61 defining the flow passage S2 is likely to be cooled by the air flow.

In the present embodiment, the flow passage S2 is defined at the position overlapping with the stator assembly 85 in the axial direction of the output shaft 81, and in the fan case 61 on the outer side portion of the stator assembly 85 in the radial direction. Accordingly, when heat is transferred to the fan case 61 from the side portion 83B of the base 82 in the vicinity of the coil 87 of the stator assembly 85, the heat is likely to be transferred to the lower fan case 63. Then, the heat transferred to the lower fan case 63 is likely to be cooled by the air flow passing through the flow passage S2 as described above.

(4) In the present embodiment, no other member is disposed between the outer peripheral surface of the pivotally support portion 84 and the rotor assembly 88, and between the stator assembly 85 and the rotor yoke 89. In other words, there is no member impeding the heat transfer from the stator assembly 85 to the rotor assembly 88, and from the rotor assembly 88 to the pivotally support portion 84. Accordingly, the heat of the coil 87 in the stator assembly 85 is likely to be transferred to the blower fan 50 through the output shaft 81.

Further, no other member is disposed between the stator assembly 85 and the rotor yoke 89. In other words, there is no member impeding the heat transfer from the stator assembly 85 to the rotor yoke 89. Accordingly, the heat of the coil 87 in the stator assembly 85 may be transferred to the blower fan 50 also through the rotor yoke 89.

(5) In the present embodiment, the blower fan 50 is constituted of the holding plate 51 and the plurality of blades 52. Further, the holding plate 51 has a shape that rises upward toward the center. When such mountain-shaped holding plate 51 is compared with a flat plate-shaped holding plate, the mountain-shaped holding plate 51 as in the present embodiment is likely to ensure a larger surface area. Further, since the plurality of blades 52 is attached to the holding plate 51, the surface area is further increased. Accordingly, the blower fan 50 of the present embodiment has high heat dissipation property.

(6) In the present embodiment, the material of the base 82 is an aluminum alloy. Accordingly, the heat transferred from the coil 87 to the side portion 83B of the base 82 is likely to be transferred to the output shaft 81 through the pivotally support portion 84.

The present embodiment may be implemented being modified as follows. The present embodiment and the following modifications may be combined with each other and implemented within a range of no technical contradiction.

In the embodiment described above, the CPAP device 10 may include another device different from the blower 40. For example, the CPAP device 10 may include a humidifier. In a case that a humidifier is provided, it is preferable that the humidifier be attached to the discharge tube 100 of the housing 20 and the hose 130 be attached to the discharge side of the humidifier, for example.

In the embodiment described above, a shape of the blower 40 is not limited to the example in the embodiment described above. For example, as long as the accommodation space for accommodating the blower fan 50 has a circular shape when viewed in the height direction Td, the outer shape of the fan case 61 may take a rectangular parallelepiped shape or a polygonal shape. Further, the lead-out tube 70 may extend in a manner that the inner diameter thereof widens, or may be curved, for example.

The shape of the fan case 61 is not limited to that in the embodiment described above. The fan case 61 may have a shape that the flow passage S2 defined inside the fan case 61 is disposed at a position not overlapping with the stator assembly 85 in the axial direction of the output shaft 81.

The fan case 61 may be omitted. In this case, it is sufficient that the housing 20 has a shape that defines a space corresponding to the flow passage S2 in the fan case 61, for example.

The configuration of the motor 80 is not limited to that in the embodiment described above. As long as the motor 80 includes the output shaft 81, the rotor assembly 88, the stator assembly 85, and the base 82, the motor 80 has no need to include other members, or may include constituents other than those in the embodiment described above.

In the embodiment described above, the base 82 may have any shape as long as being capable of supporting the output shaft 81. For example, it is acceptable that the base 82 includes only the pivotally support portion 84 and does not include the main body portion 83.

The material of the base 82 is not limited to that in the embodiment described above. However, the material of the base 82 is preferably a material having a higher thermal conductivity than the material configuring the housing 20. As a material described above, gold, silver, copper, or an alloy thereof is preferable in addition to the aluminum alloy in the embodiment described above, for example.

In the embodiment described above, another member may be disposed between the outer peripheral surface of the pivotally support portion 84 and the rotor assembly 88. Further, another member may be disposed between the rotor assembly 88 and the stator assembly 85. Note that, on an assumption of a case that other members are disposed between the outer peripheral surface of the pivotally support portion 84 and the rotor assembly 88, and between the rotor assembly 88 and the stator assembly 85, when a material with a higher heat transfer coefficient than air is adopted as the material configuring the other members, heat is likely to transfer from the stator assembly 85 to the other members.

In the embodiment described above, the number of the coils 87 is not limited.

The magnetization interval of the permanent magnet 90 having an annular shape is not required as 90 degrees in the circumferential direction as in the embodiment described above. Note that it is acceptable that the permanent magnet 90 does not have an annular shape, and a plurality of magnets is disposed on the same circumference.

In the embodiment described above, the ratio of the length of the plain bearing 91 to the output shaft 81 may be 45% or more, or less than 45%. Meanwhile, when the length of the plain bearing 91 is excessively long relative to the output shaft 81, the motor 80 may become excessively large in the height direction. Further, when the length of the plain bearing 91 is excessively short relative to the output shaft 81, there is a possibility that an expected heat dissipation effect is not achieved. Accordingly, the ratio of the length of the plain bearing 91 to the length size of the output shaft 81 is preferably approximately 40% to 50%.

The carbon material mixed in the blower fan 50 is not limited to carbon powder. For example, a substance composed substantially only of carbon atoms, such as carbon fiber or charcoal may be used.

The base material of the blower fan 50 may be a metal instead of a synthetic resin. In the case above, a material having higher thermal conductivity than a metal preferably be mixed. For example, the blower fan 50 may be formed of a material in which copper powder is mixed with aluminum.

In the embodiment described above, the shapes of the holding plate 51 and the blade 52 of the blower fan 50 are not limited. Further, the blade 52 is not required to protrude from the upper surface or the lower surface of the holding plate 51. For example, the plurality of blades 52 may be attached to a tip end of a holding plate having an annular shape.

10 CPAP DEVICE
20 HOUSING
50 BLOWER FAN
80 MOTOR
81 OUTPUT SHAFT
84A INSERTION HOLE
82 BASE
85 STATOR ASSEMBLY
87 COIL
88 ROTOR ASSEMBLY
90 PERMANENT MAGNET
91 PLAIN BEARING

The invention claimed is:

1. A continuous positive airway pressure device, comprising:
   a housing, a motor accommodated in the housing, and a blower fan rotatable by the motor,
   wherein the motor includes
   a stator assembly including a plurality of coils arranged in a circumferential direction,
   a rotor assembly including a permanent magnet and disposed in an inner side portion of the stator assembly in a radial direction,
   an output shaft fixed to the rotor assembly and configured to rotate together with the rotor assembly, and
   a base having an insertion hole into which part of the output shaft is inserted and supporting the output shaft,
   the stator assembly is fixed to the base,
   a plain bearing is interposed between an inner peripheral surface of the insertion hole and an outer peripheral surface of the output shaft, and
   the blower fan is fixed to the output shaft,
   wherein the base includes a bottomed cylindrical main body portion and a cylindrical pivotally support portion protruding from a bottom portion of the main body portion,
   an inside of the pivotally support portion forms the insertion hole, and
   an outer peripheral surface of the pivotally support portion and the rotor assembly face each other with no other member interposed therebetween, and the rotor assembly and the stator assembly face each other with no other member interposed therebetween.

2. The continuous positive airway pressure device according to claim 1,
   wherein a material of the blower fan is a mixed material of a base material comprised of a synthetic resin or a metal with a heat dissipation material having higher thermal conductivity than the base material.

3. The continuous positive airway pressure device according to claim 2,
   wherein the base material is a synthetic resin, and the heat dissipation material is a carbon material.

4. The continuous positive airway pressure device according to claim 3, further comprising:
   a fan case covering the blower fan,
   wherein a flow passage through which air from the blower fan flows is defined inside the fan case, and
   at least part of the flow passage is disposed at a position overlapping with the stator assembly in an axial direction of the output shaft and on an outer side portion of the stator assembly in the radial direction.

5. The continuous positive airway pressure device according to claim 3,
   wherein the blower fan includes a holding plate having a disk shape and a plurality of blades protruding from a surface on one side of the holding plate.

6. The continuous positive airway pressure device according to claim 2, further comprising:
   a fan case covering the blower fan,
   wherein a flow passage through which air from the blower fan flows is defined inside the fan case, and at least part of the flow passage is disposed at a position overlapping with the stator assembly in an axial direction of the output shaft and on an outer side portion of the stator assembly in the radial direction.

7. The continuous positive airway pressure device according to claim 2,
wherein the blower fan includes a holding plate having a disk shape and a plurality of blades protruding from a surface on one side of the holding plate.

8. The continuous positive airway pressure device according to claim 1, further comprising:
a fan case covering the blower fan,
wherein a flow passage through which air from the blower fan flows is defined inside the fan case, and
at least part of the flow passage is disposed at a position overlapping with the stator assembly in an axial direction of the output shaft and on an outer side portion of the stator assembly in the radial direction.

9. The continuous positive airway pressure device according to claim 8,
wherein the blower fan includes a holding plate having a disk shape and a plurality of blades protruding from a surface on one side of the holding plate.

10. The continuous positive airway pressure device according to claim 1,
wherein the blower fan includes a holding plate having a disk shape and a plurality of blades protruding from a surface on one side of the holding plate.

* * * * *